United States Patent [19]

Djuric et al.

[11] Patent Number: 5,212,198
[45] Date of Patent: May 18, 1993

[54] ALKOXY-SUBSTITUTED DIHYDROBENZOPYRAN-2-CARBOXYLIC ACIDS AND DERIVATIVES THEREOF

[75] Inventors: Stevan W. Djuric, Glenview; Thomas D. Penning, Elmhurst; James P. Snyder, Glenview, all of Ill.

[73] Assignee: G. D. Searle & Co., Chicago, Ill.

[21] Appl. No.: 958,632

[22] Filed: Oct. 9, 1992

Related U.S. Application Data

[62] Division of Ser. No. 759,272, Sep. 13, 1991, which is a division of Ser. No. 521,777, May 10, 1990, Pat. No. 5,073,562.

[51] Int. Cl.$^5$ .................. A61K 31/415; C07D 405/12
[52] U.S. Cl. ..................................... 514/397; 548/311.4
[58] Field of Search ...................... 548/311.4; 514/397

[56] References Cited

U.S. PATENT DOCUMENTS

| | | | |
|---|---|---|---|
| 3,882,148 | 5/1975 | Augstein et al. | 260/345.2 |
| 4,281,008 | 7/1981 | Chamberlain et al. | 424/269 |
| 4,546,194 | 10/1985 | Miyano et al. | 549/401 |
| 4,565,882 | 1/1986 | Miyano et al. | 549/399 |
| 4,665,203 | 5/1987 | Miyano et al. | 549/402 |
| 4,778,903 | 10/1988 | Miyano et al. | 549/399 |
| 4,788,214 | 11/1988 | Cohen | 514/456 |
| 4,889,871 | 12/1989 | Djuric et al. | 514/456 |

FOREIGN PATENT DOCUMENTS

| | | |
|---|---|---|
| 0017332 | 2/1980 | European Pat. Off. |
| 0150447 | 12/1984 | European Pat. Off. |
| 0129906 | 1/1985 | European Pat. Off. |
| 0079637 | 1/1987 | European Pat. Off. |
| 60-42378 | 2/1987 | Japan . |

OTHER PUBLICATIONS

R. A. Appleton et al. Antagonists of Slow Reacting Substance of etc. J. Med. Chem., 20(3), 371–379, Jan. 1977.

Chem. Abstracts Service AN:CA, vol. 103 (19), 160389g Nov. 1985.
Chem. Abstracts, vol. 97, No. 3, 16 807g Jul. 1982.

Primary Examiner—Mary C. Lee
Assistant Examiner—Lenora A. Miltenberger
Attorney, Agent, or Firm—Cynthia S. Kovacevic; Paul D. Matukaitis; Roger A. Williams

[57] ABSTRACT

This invention relates to compounds of Formula I and the stereoisomers and pharmaceutically acceptable salts thereof

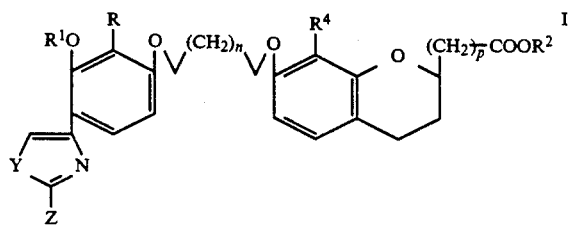

wherein
R is alkyl, alkenyl, alkynyl, or $(CH_2)_m R^3$ where $R^3$ is cycloalkyl and m is 1 or 2;
$R^1$ is alkyl;
$R^2$ is hydrogen or alkyl;
$R^4$ is alkyl;
n is an integer from 1 to 5;
p is an integer from 0 to 6;
Y is NH, oxygen or sulfur; and
Z is hydrogen, alkyl, alkoxy, $NR^4R^5$ wherein $R^4$ and $R^5$ are independently hydrogen or alkyl, or $SR^6$ wherein $R^6$ is hydrogen, benzyl or alkyl.

The compounds of Formula I are leukotriene $B_4$ antagonists and are useful as anti-inflammatory agents and in the treatment of leukotriene $B_4$ mediated conditions.

15 Claims, No Drawings

ALKOXY-SUBSTITUTED DIHYDROBENZOPYRAN-2-CARBOXYLIC ACIDS AND DERIVATIVES THEREOF

This is a division, of application Ser. No. 07/759,272, filed Sep. 13, 1991, which is a divisional of U.S. Ser. No. 07/521,777 filed on May 10, 1990, now U.S. Pat. No. 5,073,562.

BACKGROUND OF THE INVENTION

1. Field Of The Invention

This invention is in the field of pharmaceutical agents which selectively act as leukotriene $B_4$ ($LTB_4$) antagonists.

2. Prior Art

Leukotriene $D_4$ and $C_4$ ($LTD_4/LTC_4$) and leukotriene $B_4$ ($LTB_4$) are products of the arachidonic acid metabolic pathway. $LTD_4$ and $LTC_4$ are associated with smooth muscle contraction and contract guinea pig ileum, human and guinea pig bronchi and human pulmonary artery and vein. $LTB_4$ is associated with neutrophil stimulation which is characterized by chemotaxis, aggregation and degranulation. $LTB_4$ is believed to be an important mediator of inflammation. High levels of $LTB_4$ are detected in rheumatoid arthritis, gout, psoriasis, and inflammatory bowel disease. Thus antagonists of $LTB_4$ are useful in the therapy of such diseases.

*Gastroenterology,* 1985: 88: 580–7 discusses the role of arachidonic acid metabolites in inflammatory bowel disease.

*British Medical Bulletin,* (1983), vol. 39, No. 3, pp 249–254, generally discusses the pharmacology and pathophysiology of leukotriene $B_4$.

*Biochemical and Biophysical Research Communications,* Vol. 138, No. 2 (1986), pp. 540–546 discusses the pharmacology of a specific $LTB_4$ antagonist which has a different structure than compounds of this invention.

U.S. Pat. No. 4,889,871 discloses alkoxy-substituted dihydrobenzopyran-2-carboxylate derivatives which are selective antagonists of $LTB_4$ with little or no antagonism of $LTD_4$ and are useful as antiinflammatory agents for treating inflammatory bowel disease.

BRIEF DESCRIPTION OF THE INVENTION

This invention encompasses compounds of Formula I and the stereoisomers and pharmaceutically acceptable salts thereof;

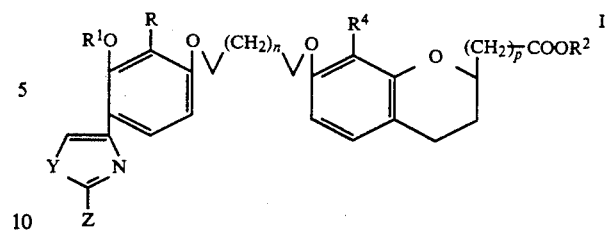

wherein
R represents alkyl having 2 to 6 carbon atoms, alkenyl having 2 to 6 carbon atoms, alkynyl having 2 to 6 carbon atoms, or $-(CH_2)_m-R^3$ wherein $R^3$ represents cycloalkyl of 3 to 5 carbons atoms and m is 1 or 2;
$R^1$ represents alkyl having 1 to 4 carbon atoms;
$R^2$ represents hydrogen or alkyl having 1 to 5 carbon atoms;
$R^4$ represents alkyl of 1 to 6 carbon atoms;
n is an integer from 1 to 5;
p is an integer from 0 to 6;
Y represents NH, oxygen or sulfur; and
Z represents hydrogen, alkyl having 1 to 4 carbon atoms, alkoxy having 1 to 4 carbon atoms, $NR^4R^5$ wherein $R^4$ and $R^5$ are independently hydrogen or alkyl having 1 to 4 carbon atoms, or $SR^6$ wherein $R^6$ is hydrogen, benzyl or alkyl having 1 to 4 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, asthma, multiple sclerosis, and psoriasis and in treating conditions mediated by $LTB_4$.

DETAILED DESCRIPTION OF THE INVENTION

This invention encompasses the compounds of formula I as previously described.

Preferred embodiments of the present invention are compounds of the formula Ia, the stereoisomers and pharmaceutically acceptable salts thereof,

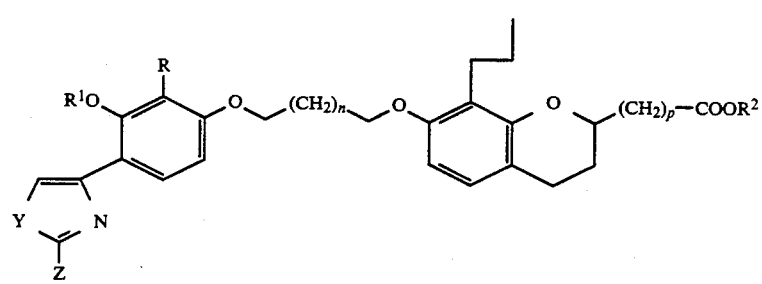

wherein
R represents alkyl having 2 to 4 carbon atoms alkenyl having 3 to 4 carbon atoms, or cyclopropylalkyl wherein the alkyl moiety has 1 to 2 carbon atoms;
$R^1$ represents methyl or ethyl;
$R^2$ represents hydrogen or alkyl having 1 to 3 carbon atoms;
n is an integer from 1 to 3;
p is an integer from 0 to 4;
Y represents NH, oxygen or sulfur; and Z represents hydrogen, alkyl having 1 to 4 carbon atoms, alkoxy having 1 to 4 carbon atoms, $NH_2$, or $SR^6$ wherein $R^6$ is hydrogen, benzyl or alkyl of 1 to 4 carbon atoms.

These compounds are selective antagonists of leukotriene $B_4$ ($LTB_4$) with little or no antagonism of leukotriene $D_4$ ($LTD_4$) and are useful anti-inflammatory agents for treating inflammatory bowel disease, rheumatoid arthritis, gout, and psoriasis.

More preferred embodiments are compounds of the formula II and the stereoisomers and pharmaceutically acceptable salts thereof

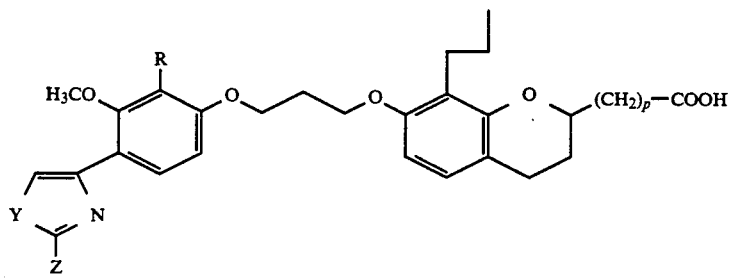

II wherein R represents propyl, 2-propenyl, or cyclopropylmethyl; p is an integer from 0 to 2; Y represents NH, oxygen, or sulfur; and Z represents hydrogen, $NH_2$, alkyl having 1 to 2 carbon atoms, alkoxy having 1 to 2 carbon atoms or $SR^6$ wherein $R^6$ is hydrogen, benzyl or methyl.

Alkyl defined for R, $R^1$, $R^2$, $R^3$ and $R^4$ is straight or branched chain alkyl having the indicated number of carbon atoms.

Pharmaceutically acceptable salts such as ammonium, sodium, potassium, alkaline earth, tetraalkylammonium and the like are encompassed by the invention.

Schemes A, B, and C show general methods for preparing compounds of the invention.

In Scheme A, the imidazoles are prepared using an appropriate α-haloketone and 2-benzyl-2-thiopseudourea hydrochloride. The ester (III) is converted to its silyl enol ether and reacted with a halogenating reagent [i.e., an N-halosuccinimide (NXS)] to give the 4-(2-halo-1-oxoethyl)alkyl ester (IV) which is then reacted with 2-benzyl-2-thiopseudourea hydrochloride to give the 4-[2-(phenylmethyl)thio]-1H-imidazol-4-yl alkyl ester (V). Hydrolysis of (V) with lithium hydroxide or other suitable base gives the acid (VI). Alternately, reduction of (V) under alkaline conditions gives (VII).

In Scheme B, condensation of ketone (VIII) with an appropriate amide or thioamide gives the appropriately substituted thiazoles or oxazoles (IX) wherein Y=S or O. Hydrolysis of (IX) with lithium hydroxide or another suitable base, gives the acid (X). Alternately when Z in (IX) is —SH, then alkylation of (IX) with a alkyl halide ($AlkX^1$) gives the thioalkyl compound (XI) which can be hydrolyzed to the acid with an appropriate base.

Scheme C shows an alternate synthesis for the substituted thiazoles in which IV is reacted with a thiocyanate to give the 4-(1-oxo-2-thiocyanatoethyl) compound (XIII) which is then reacted with $Z^-$ where Z may be alkoxy, —SR, —$NH_2$ to give (XIV) followed by reaction with an appropriate base such as lithium hydroxide to give the acid product (XV).

Reaction of the acid with an appropriate base gives the salt.

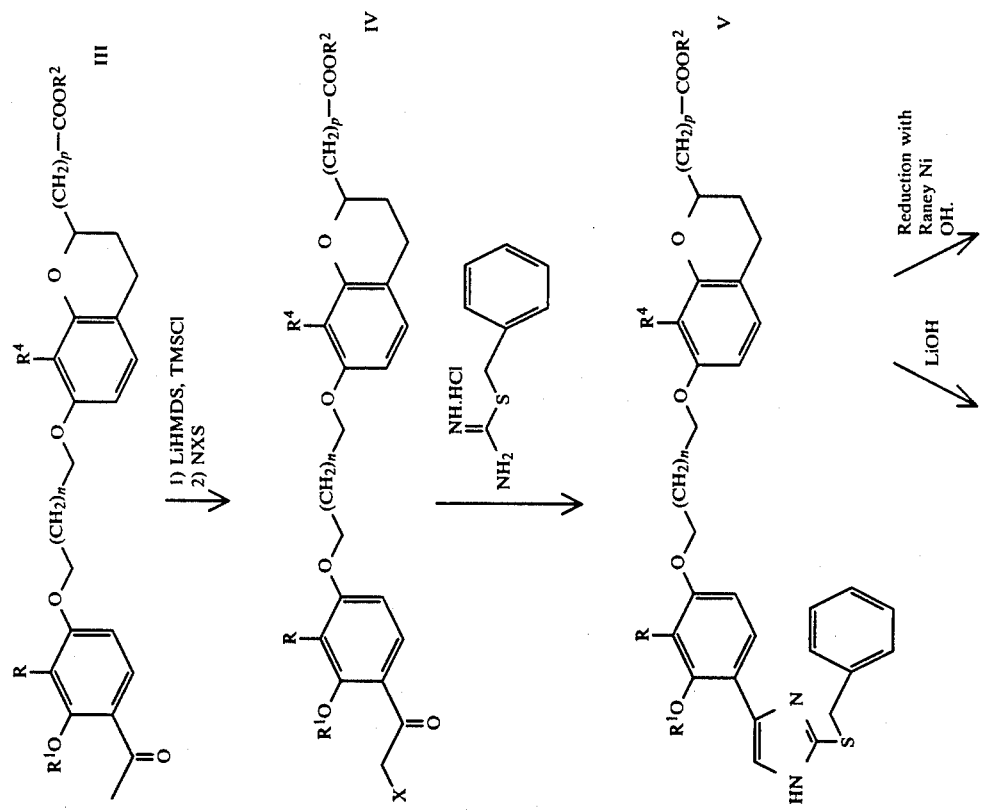

-continued
Scheme A
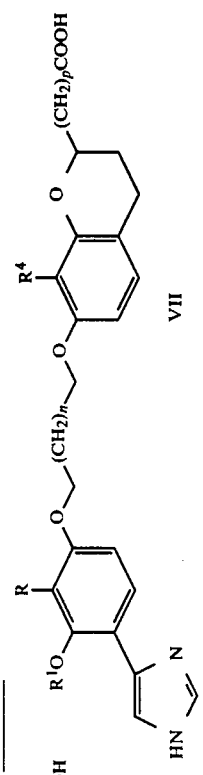
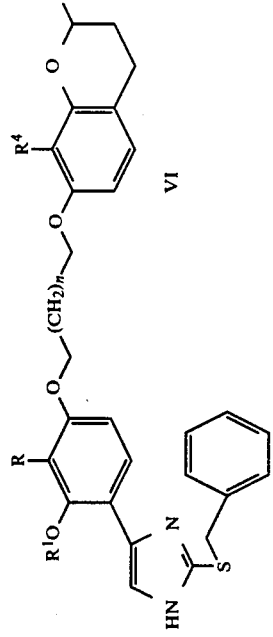
$R^2$ = alkyl
Alk = alkyl
X = halogen, preferably Cl
$R^4$ = alkyl

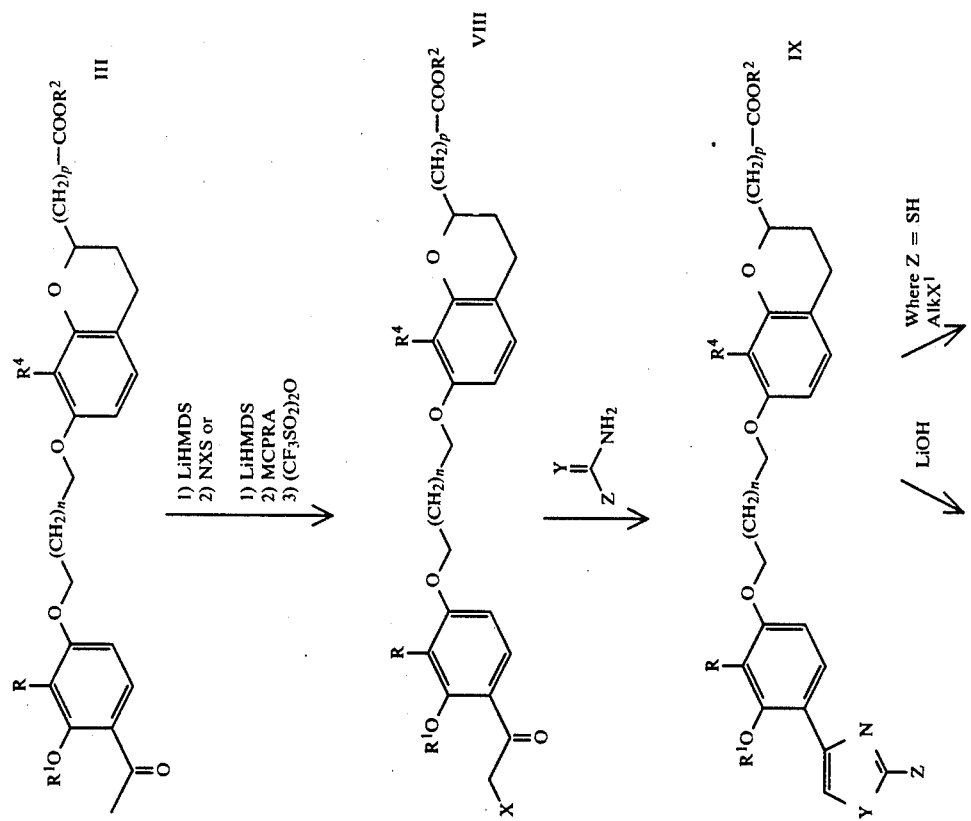

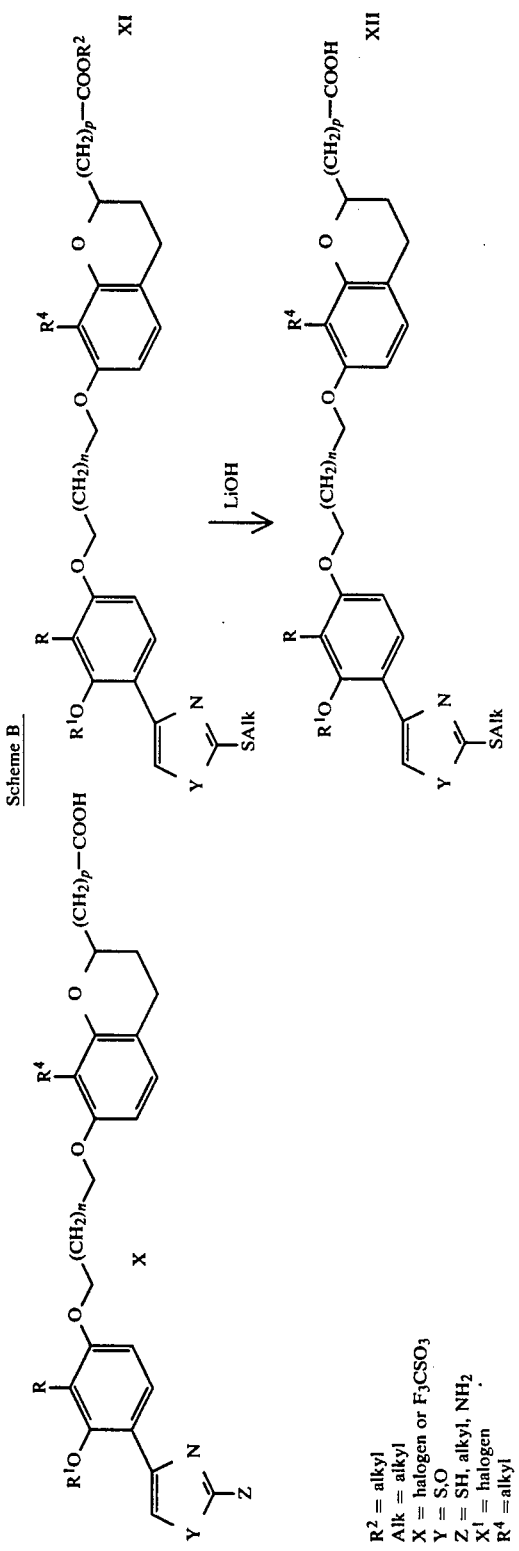
Scheme B -continued
$R^2$ = alkyl
Alk = alkyl
X = halogen or $F_3CSO_3$
Y = S,O
Z = SH, alkyl, $NH_2$
$X^1$ = halogen
$R^4$ = alkyl

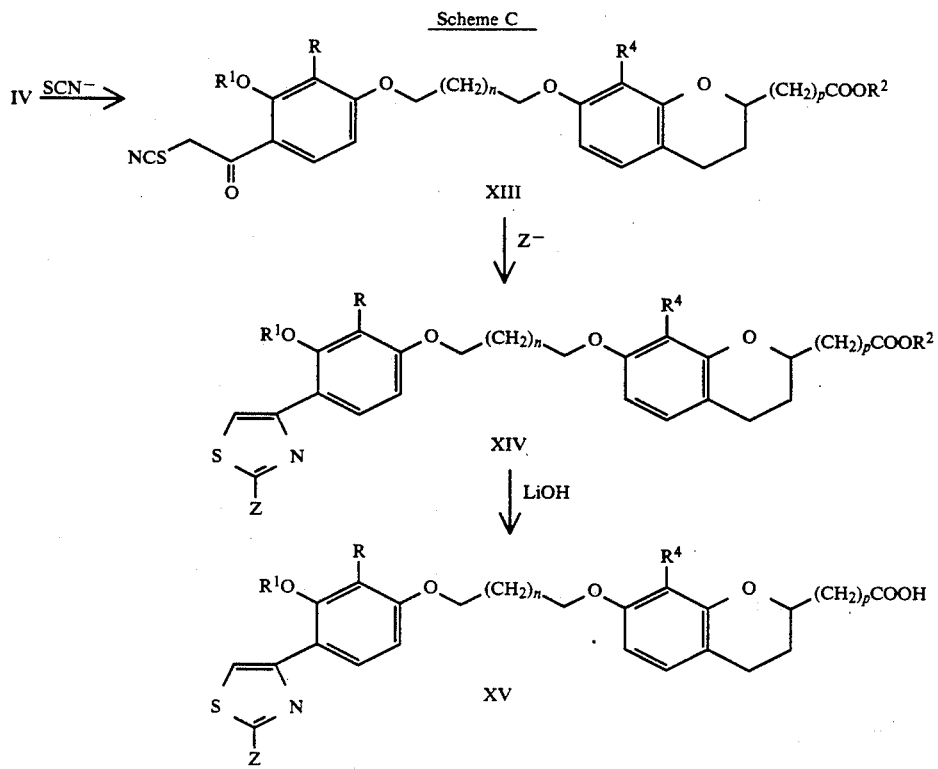

Scheme C

R² = Alkyl
Z = alkoxy, —SR, —NH₂
R⁴ = alkyl

The biological activity of compounds of this invention is indicated by the following tests.

Preparation of Human Neutrophils

Neutrophils were purified from venous blood of normal human donors using standard techniques of dextran sedimentation, centrifugation on Ficoll-paque ® (Pharmacia) or Histopaque ® sterile solution (Sigma) and hypotonic lysis of erythrocytes (Boyum, A., *Isolation of Leukocytes From Human Blood: Further Observations. Scand. J. Lab. Clin. Invest.*, 21 (Suppl. 97): 31, 1968). The purity of isolated neutrophils was >95%.

LTB₄ Receptor Binding Assay

Neutrophils ($4\text{-}6\times 10^6$) in 1 ml Hanks' balanced salt solution (HBSS) containing 10 mM HEPES buffer, pH 7.4 and 20 mM nordihydroguaiaretic acid were incubated with $0.6\times 10^{-9}$M ($^3$H) LTB₄ in the presence or absence of test compounds. The incubation was carried out at 0° C. for 45 minutes and terminated by adding 5 ml of ice-cold HBSS followed by rapid filtration of the incubation mixture under vacuum through GF/C glass fiber filters. The filters were further washed with 10 ml HBSS and radioactivity was determined. Specific binding was defined as the difference between total binding and nonspecific binding which was not displaced by $10^{-7}$M unlabeled LTB₄. All data refer to specific binding.

Modified Boyden Chamber Chemotaxis

Human neutrophils were isolated from citrated peripheral blood using standard techniques of dextran sedimentation, followed by centrifugation on Histopaque ® sterile solution (Sigma) or Ficoll-paque ® (Pharmacia) and hypotonic lysis of erythrocytes. A final cell suspension of $3.4\times 10^6$ neutrophils/ml of HEPES-buffered Hanks' balanced salt solution (HBSS, pH 7.3) was added to the upper well (0.8 ml) of a modified Boyden chamber (blind well). The lower well (0.2 ml), separated by a polycarbonate membrane (Nucleopore Corp.), contained HBSS or $3\times 10^{-8}$M LTB₄ in the presence or absence of test compound. Following a 40–90 minute incubation at 37° C. in 5% CO₂-95% air, cells from the lower well were lysed and nuclei counted in a Model S-Plus-IV Coulter Counter. The number of neutrophils migrating into the lower chamber in the absence of chemoattractant was subtracted from the number of cells migrating in the presence of a chemoattractant. Inhibition of chemotaxis by test compounds was expressed as percent inhibition relative to uninhibited control.

Results for representative compounds of the invention are shown in Table 1.

Data are expressed as potency relative to the compound of Example 1(b), 7-[3,(4-acetyl-3-methoxy-2-propylphenoxy) propoxy]-3,4-dihydro-8-propyl-2H-1-benzopyran-2-carboxylic acid, which is disclosed in U.S. Pat. No. 4,889,871.

TABLE 1

| | Relative Potency Values for LTB₄ Antagonists[1] | | |
|---|---|---|---|
| Compound | LTB₄ Receptor Binding | Chemotaxis | |
| | | LTB₄ | fMLP |
| Example 1 (b) | 1.0 (0.3 μM) | 1.0 (1.8 μM) | 1.0 (5.4 μM) |
| Example 5 | 4.0 | 2.2 | 0.73 |
| Example | 2.65 | 1.86 | 2.0 |

TABLE 1-continued

Relative Potency Values for LTB₄ Antagonists[1]

| Compound | LTB₄ Receptor Binding | Chemotaxis | |
|---|---|---|---|
| | | LTB₄ | fMLP |
| Example 8 | | | |
| Example 9 | 1.0 | 0.66 | 0.45 |
| Example 10 | 1.56 | 0.63 | 1.4 |
| Example 12 | 4.5 | 3.0 | 1.1 |
| Example 14 | 0.47 | <0.1 | — |
| Example 17 | 11.6 | 8.3 | 1.9 |
| Example 21 | 9.5 | 9.6 | 2.4 |
| Example 24 | 0.31 | <<0.23 | — |
| Example 26 | 0.51 | — | — |
| Example 28 | 0.19 | 0.05 | — |
| Example 29 | 0.02 | IA | — |

IA = Inactive at the dose tested.
[1]Data are expressed as potency relative to a known LTB₄ antagonist, the compound of Example 1 (b), defined as 1.0. Values in the parentheses refer to IC₅₀ values (μM) for the compound of Example 1 (b).

The compounds of this invention can be administered in a number of dosage forms. A preferred method of delivery would be oral or in such a manner so as to localize the action of the antagonist. In an inflammatory condition such as rheumatoid arthritis the compounds could be injected directly into the affected joint. The compounds could also be administered in oral unit dosage forms such as tablets, capsules, pills, powders or granules. They may be introduced intraperitoneally, subcutaneously, or intramuscularly using forms known to the pharmaceutical art. Topical application in the form of salves and ointments are useful for treating psoriasis. Regardless of the route of administration selected, the compounds are formulated into pharmaceutically acceptable dosage forms by conventional methods known to the pharmaceutical art.

The compounds may be administered in a number of dosage forms, for example, such oral dosage forms as tablets, capsules, pills, powders, or granules. They may also be administered intravascularly, intraperitoneally, subcutaneously, topically or intramuscularly using forms known to the pharmaceutical art.

In general, a unit dosage of a compound of the invention would contain from about 50 mg to about 500 mg of the active ingredient with from about 70 mg to about 300 mg preferred.

An effective but non-toxic quantity of the compound is employed in treatment. The dosage regimen for antagonism of LTB₄ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained. Generally, a dosage range of 1 to 25 mg/kg of body weight is administered to patients in need of treatment for inflammatory conditions.

The following examples illustrate the preparation of compounds of this invention from known starting materials. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

U.S. Pat. No. 4,665,203 issued May 12, 1987 incorporated herein by reference, U.S. Pat. No. 4,889,871, incorporated herein by reference, and European Application EP 0292977 published Nov. 30, 1988 disclose methods for making some of the intermediates used in making compounds of the present invention.

EXAMPLE 1

(a) Methyl 7-[3-(4-acetyl-3-methoxy-2-propylphenoxy) propoxy]-3,4-dihydro-8-propyl-2H-1-benzopyran-2-carboxylate

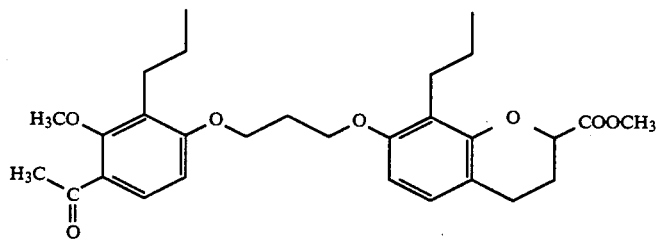

1a

Methyl 7-[3-(4-acetyl-3-hydroxy-2-propyl-phenoxy)-propoxy]-3,4-dihydro-8-propyl-2H-1-benzopyran-2-carboxylate (493 mg) was added to 25 ml of acetone containing 276 mg of anhydrous potassium carbonate and 282 mg of methyl iodide. The mixture was refluxed for about 24 hours and water was added and the mixture was then extracted with ethyl acetate. The extract was dried, the solvent removed under vacuum, and the residual oil was chromatographed over silica gel with a 40/60 mixture of ethyl acetate/hexane to provide pure methyl ether, methyl 7-[3-(4-acetyl-3-methoxy-2-propylphenoxy)propoxy]-3,4-dihydro-8-propyl-2H-1-benzopyran-2-carboxylate.

Example 1(b)

7-[3-(4-acetyl-3-methoxy-2-propylphenoxy)propoxy]-3,4-dihydro-8-propyl-2H-1-benzopyran-2-carboxylic acid

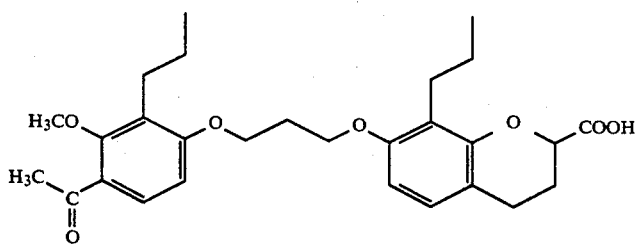

1(b)

(b) The methyl ether (1a) (340 mg) was dissolved in methanol (5 ml) containing lithium hydroxide (0.7 ml of a 2N LiOH solution in water). The mixture was stirred at room temperature overnight and the solvent removed in vacuo. The residue was partitioned between ethyl acetate and 2N HCl and the organic layer separated and washed with brine. Evaporation of the volatiles in vacuo afforded crude acid of Formula III. This material was purified by silica gel chromatography using ethyl acetate/hexane/acetic acid (40:60:0.5) as eluant. The pure product was recrystallized from ethyl acetate/hexane to afford 200 mg of product, 7-[3-(4-acetyl-3-methoxy-2-propylphenoxy)propoxy]-3,4-dihydro-8-propyl-2H-1-benzopyran-2-carboxylic acid, m.p. 65°–68° C.

Microanalysis: Found: C 69.22, H 7.53. Theory: C 69.40, H 7.49.

trated under vacuum. The crude enol ether residue was stirred in 10 ml of methylene chloride at 0° C. and 0.26 g of 80–85% m-chloroperbenzoic acid (MCPBA) (about 1.2 mmol) was added in portions and the mixture was stirred at 0° C. for 1 hour. The reaction mixture was diluted with hexane, filtered, and concentrated under vacuum. Flash chromatography on silica gel using 20:1 to 1:1 hexane/ethyl acetate provided the product (0.304 g, 0.59 mmol), 49%, melting point 87–88° C.

Analysis for $C_{29}H_{38}O_8$ (MW=514.621):
Calcd: C, 67.69; H, 7.44
Found: C, 67.90; H, 7.67

EXAMPLE 3

Methyl 7-[3-(4-(2-trifluoromethylsulfonyloxy-1-oxoethyl)-3-methoxy-2-propylphenoxy)propoxy]-3,4-dihydro-8-propyl-2H-1-benzopyran-2-carboxylate.

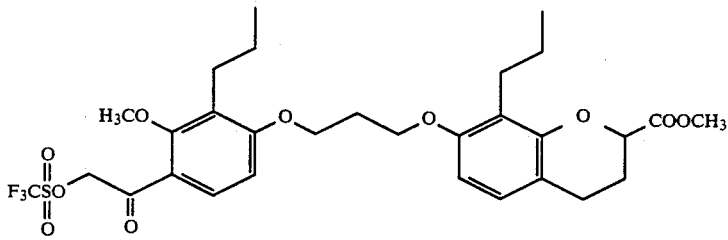

The NMR (CDCl₃) shows a —OCH₃ at δ3.75.

EXAMPLE 2

Methyl 7-[3-(4-(2-hydroxy-1-oxoethyl)-3-methoxy-2-propylphenoxy)propoxy]-3,4-dihydro-8-propyl-2H-1-benzopyran-2-carboxylate

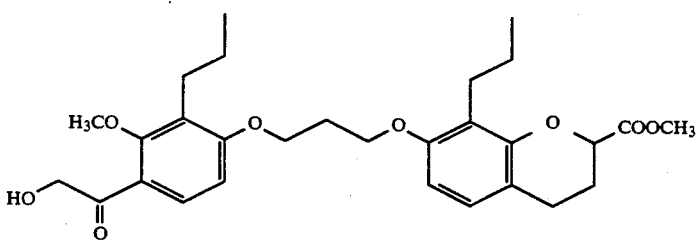

Compound 1a from Example 1 (0.605 g, 1.21 mmol) was stirred in 10 ml tetrahydrofuran (THF) at −78° C. and 1.3 ml of 1M lithium hexamethyldisilazide (LiHMDS) in THF was added and the reaction mixture was stirred at −78° C. for 5 minutes. Trimethylsilyl chloride (TMSCl) (0.25 ml, 1.97 mmol) was added and the mixture was stirred at 0° C. for 15 minutes. The mixture was diluted with hexane, filtered, and concen- The compound of Example 2 (0.41 g, 0.80 mmol) in 6.0 ml of methylene chloride was stirred at −78° C. Trifluoromethylsulfonic anhydride (0.20 ml, 1.17 mmol) was added followed by 2,6-dimethylpyridine (0.14 ml, 1.17 mmol). The mixture was stirred at −78° C. for 50 minutes and then poured into ethyl ether/water. The ether layer was washed with brine, dried over sodium sulfate, and concentrated under vacuum to give the product as a white solid.

EXAMPLE 4

Methyl 3,4-Dihydro-7-[3-[3-methoxy-4-(4-oxazolyl)-2-propylphenoxy]propoxy]-8-propyl-2H-1-benzopyran-2-carboxylate

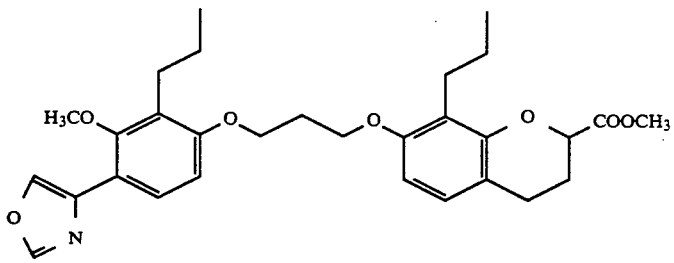

The compound of Example 3 (0.10 g, 0.155 mmol) was stirred with 0.5 ml of formamide and 0.2 ml of dimethyl formamide (DMF) for 1.5 hours at 170° C. The reaction mixture was cooled and poured into ethyl acetate/water. The ethyl acetate layer was washed with brine, dried over sodium sulfate, and concentrated under vacuum. The residue was flash chromatographed on silica gel using 10:1 to 4:1 hexane/ethyl acetate eluant to give the produce, 0.057 g (0.109 mmol), 35%.

Analysis calculated for $C_{30}H_{37}NO_7$ (MW=523.63):
Calculated: C, 68.81; H, 7.12, N, 2.67
Found: C, 68.94; H, 7.34, N, 2.46

EXAMPLE 5

3,4-Dihydro-7-[3-[3-methoxy-4-(4-oxazolyl)-2-propylphenoxy]propoxy]-8-propyl-2H-1-benzopyran-2-carboxylic acid

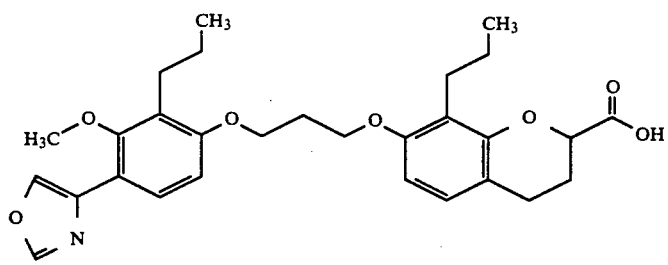

The compound of Example 4 (25 mg, 47.7 μmol) along with 1.0 ml of 4:1 methanol/THF, and 0.09 ml of 1N lithium hydroxide were stirred at 0° C. for thirty minutes. An additional 0.09 ml of 1N lithium hydroxide was added and the reaction mixture was stirred at room temperature for 45 minutes. The reaction mixture was poured into 0.5N hydrochloric acid/ethyl acetate. The ethyl acetate layer was washed with brine, dried over sodium sulfate, and concentrated under vacuum to give the product; melting point 136–139° C. High resolution mass spectrum m/e 510.2471 (calculated for $C_{29}H_{36}NO_7$ (M+H), 510.2492).

EXAMPLE 6

Methyl 7-[3-(4-(2-chloro-1-oxoethyl)-3-methoxy-2-propylphenoxy)propoxy]-3,4-dihydro-8-propyl-2H-1-benzopyran-2-carboxylate

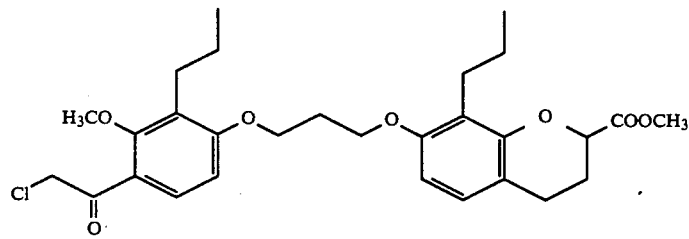

The compound of Example 1a (2.48 g, 4.97 mmol) in 50 ml THF was stirred at −78° C. and 5.5 ml of 1M lithium hexamethyldisilazide in THF was added. The reaction mixture was stirred at −78° C. for 15 minutes and then trimethylsilyl chloride (1.27 ml, 10.0 mmol) was added, and the reaction mixture was stirred at 0° C. for 15 minutes. The mixture was concentrated, dissolved in hexane, filtered, and concentrated. The crude enol ether was stirred in 50 ml of THF and cooled to 0° C. N-Chlorosuccinimide (NCS) (0.73g, 5.5 mmol) was added, and the mixture was stirred at room temperature for 15 min. then 6.0 ml of 1N tetra-butylammonium fluoride in THF was added, and the mixture was stirred at room temperature for 5 min. The mixture was poured into ethyl ether/water, and the ether layer was washed with brine, dried over sodium sulfate and concentrated. F)ash chromatography on silica gel using 20:1 to 10:1 hexane/ethyl acetate provided 1.53 g (2.87 mmol), 87% yield of product, melting point 47–49° C.

Analysis calculated for $C_{29}H_{37}O_7Cl$ (533.067)
Calculated: C, 65.34; H, 7.00 .
Found: C, 64.99; H, 7.06
High resolution mass spectrum, m/e 532.2249 (calculated for $C_{29}H_{37}O_7$ $^{35}Cl$, 532.2228).

EXAMPLE 7

Methyl 3,4-dihydro-7-[3-[3-methoxy-4-[2-[(phenylmethyl)-thio]-1H-imidazol-4-yl]-2-propylphenoxy]-propoxy]-8-propyl-2H-1-benzopyran-2-carboxylate

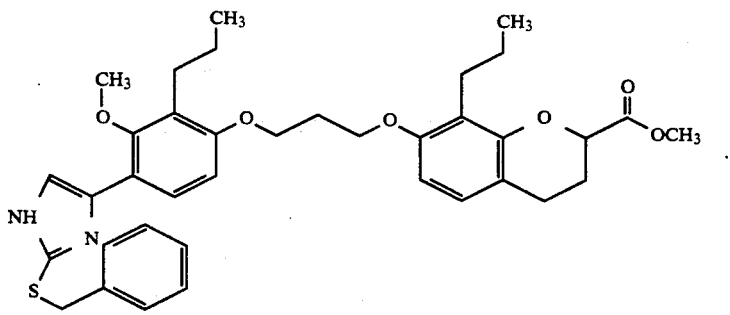

The compound of Example 6 (19 mg, 35.6 μmol) along with sodium iodide (2 mg, 13.3 μmol) and sodium carbonate (20.0 mg, 189 μmol) in 0.5 ml dimethylformamide (DMF) were stirred with 2-benzyl-2-thiopseudourea hydrochloride (9.0 mg, 44.4 μmol). The reaction mixture was heated to 80° C. for 5 minutes then cooled and poured into ethyl ether/water. The ether layer was washed with brine, dried over sodium sulfate, and concentrated under vacuum. Flash chromatography of the residue on silica gel with 3:1 hexane/ethyl acetate as eluant gave the product in 78% yield. High resolution mass spectrum, m/e 644.2918 (calculated for $C_{37}H_{44}O_6N_2S$, 644.2920).

EXAMPLE 8

3,4-Dihydro-7-[3-[3-methoxy-4-[2-[(phenylmethyl)thio]-1H-imidazol-4-yl]-2-propylphenoxy]propoxy]-8-propyl-2H-1-benzopyran-2-carboxylic acid

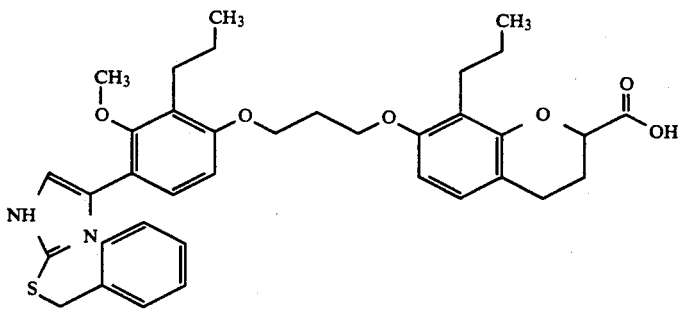

The compound of Example 7 (12.0 mg, 18.6 μmol) in 1.0 ml of 4:1 methanol/THF and 40 ml of 1N lithium hydroxide was stirred at room temperature for 2.5 hours. The reaction mixture was poured into 0.5N hydrochloric acid/ethyl acetate. The ethyl acetate layer was washed with brine, dried over sodium sulfate, and concentrated under vacuum. Flash chromatography of the residue using 3:1 to 1:1 hexane/ethyl acetate (1% acetic acid) as eluant gave the product; melting point 92-97° C. High resolution mass spectrum, m/e 586.2868 (Calculated for $C_{35}H_{42}O_4N_2S$ (M-CO$_2$), 586.2865).

EXAMPLE 9

3,4-Dihydro-7-[3-[4-(1H-imidazol-4-yl)-3-methoxy-2-propylphenoxy]propoxy]-8-propyl-2H-1-benzopyran-2-carboxylic acid

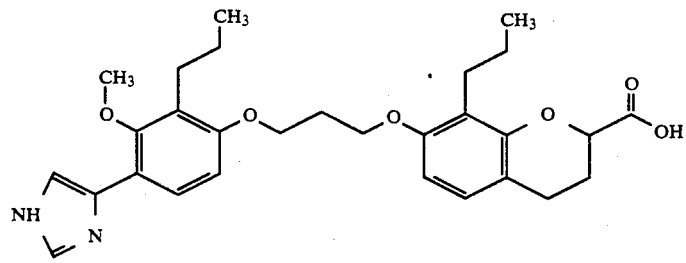

The compound of Example 7 (35.0 mg, 54 μmol) along with ethanol (1.0 ml), 50% sodium hydroxide (0.5 ml), water (0.75 ml), and 0.5 g of 50% Raney nickel catalyst and water were heated at reflux for 2.5 hours. The reaction mixture was cooled, filtered and concentrated under vacuum. The residue was dissolved in ethyl acetate and washed with 0.5N hydrochloric acid and brine, dried over sodium sulfate, and concentrated under vacuum to give the product.

EXAMPLE 10

7-[3-[4-(2-amino-4-thiazolyl)3-methoxy-2-propylphenoxy]propoxy]3,4-dihydro-8-propyl-2H-1-benzopyran-2-carboxylic acid

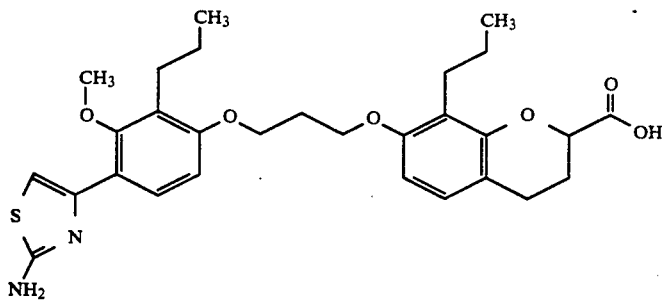

Methyl 7-[3-[4-(2-chloro-1-oxoethyl)-3-methoxy-2-propylphenoxy]propoxy]-3,4-dihydro-propyl-2-H-1-benzopyran-2carboxylate (0.13 g, 0.244 mmol), 5 mL ethanol, 1 mL H₂O, and thiourea (22 mg, 0.29 mmol) were combined and refluxed for 4 hrs. The reaction mixture was cooled, and 1 mL of 5M sodium hydroxide was added. The reaction mixture was stirred at room temperature for 10 min., and poured into 0.5N hydrochloric acid/methylene chloride. The methylene chloride layer was washed with brine, dried over sodium sulfate and concentrated. Flash chromatography of the concentrate on silica gel using 2:1 to 1:2 hexane/ethyl acetate (1% acetic acid) gave the product (0.125 g, 0.231 mmol, 95% yield). High resolution mass spectrum, m/e 541.2379 (calculated for C₂₉H₃₇N₂O₆S (M+H), 541.2372).

EXAMPLE 11

Methyl 3,4-dihydro-7-[3-[3-methoxy-2-propyl-4-(4-thiazolyl)phenoxy]propoxy]-8-propyl-2H-1-benzopyran-2-carboxylate

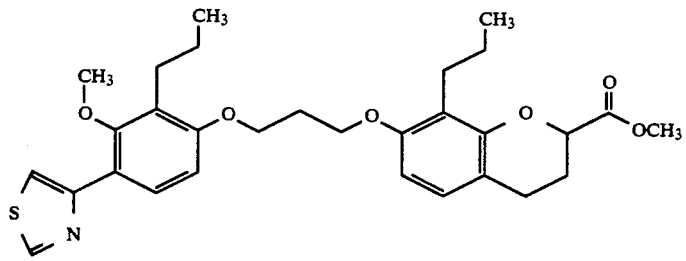

Formamide (24 mL, 0.69 mmol), phosphorus pentasulfide (54 mg, 0.123 mmol) and 4 mL of dioxane were refluxed for 30 min. Methyl 7-[3-[4-(2-chloro-1-oxoethyl)-3-methoxy-2-propylphenoxy]propoxy]-3,4-dihydro-8-propyl-2H-1-benzopyran-2-carboxylate (30 mg, 0.056 mmol) in 0.5 mL dioxane was added along with 50 mg magnesium carbonate, and the mixture was refluxed for 18 hr. The reaction mixture was poured into ethyl ether/0.5N sodium hydroxide, and the ether layer was washed with brine, dried over sodium sulfate, and concentrated. Flash chromatography of the concentrate using 10:1 hexane/ethyl acetate as eluant provided the product (30 mg, 0.055 mmol, 99% yield). High resolution mass spectrum, m/e 539.2335 (calculated for C₃₀H₃₇SO₆N, 539.2341).

EXAMPLE 12

3,4-dihydro-7-[3-[3-methoxy-2-propyl-4-(4-thiazolyl)phenoxy]-propoxy]-8-propyl-2H-1-benzopyran-2-carboxylic acid

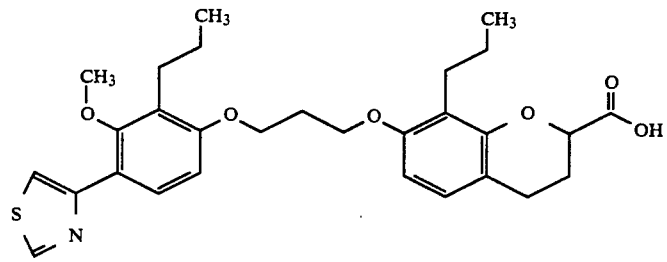

The compound of Example 11 (27 mg, 50 mmol) was combined with 2 mL of 4:1 methanol/THF and 0.1 mL of 1N lithium hydroxide, and the mixture was allowed to react at room temperature for 3 hr (another 0.05 mL LiOH was added after 1.5 hr). The reaction mixture was poured into ethyl acetate/0.5M hydrochloric acid, and the ethyl acetate layer was washed with brine, dried over sodium sulfate and concentrated under vacuum to give the product. High resolution mass spectrum, m/e 481.2281 (calculated for C₂₈H₃₅SO₄N (M-CO₂), 481.2287).

EXAMPLE 13

Methyl 3,4-dihydro-7-[3-[3-methoxy-4-(2-methyl)-4-oxazolyl)-2-propylphenoxy]propoxy]-8-propyl-2H-1-benzopyran-2-carboxylate

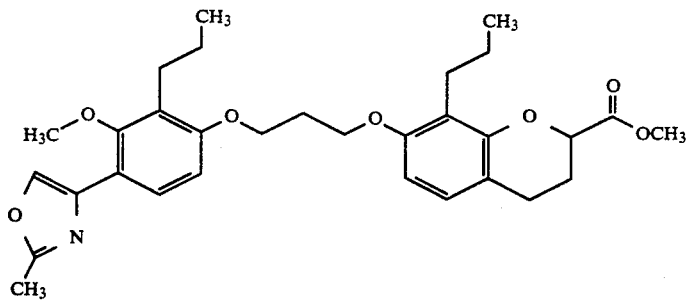

Methyl 7-[3-[4-(2-chloro-1-oxoethyl)-3-methoxy-2-propylphenoxy]propoxy]-3,4-dihydro-8-propyl-2H-1-benzopyran-2-carboxylate (0.105 g, 0.197 mmol) was combined with about 50 mg urea (about 0.8 mmol), and 3 mL acetic acid, and the reaction mixture was heated to about 120° C. for 47 hr. The reaction mixture was poured into ethyl acetate/water, and the ethyl acetate layer was washed with brine, dried over sodium sulfate, and concentrated. Flash chromatography on silica gel using 10:1 to 5:1 hexane/ethyl acetate as eluant provided 37 mg (0.064 mmol); 32% yield of the product. High resolution mass spectrum, m/e 537.2728 (calculated for $C_{31}H_{39}NO_7$, 537.2726).

EXAMPLE 14

3,4-dihydro-7-[3-[3-methoxy-4-(2-methyl-4-oxazolyl)-2-propylphenoxy]propoxy]-8-propyl-2H-1-benzopyran-2-carboxylic acid

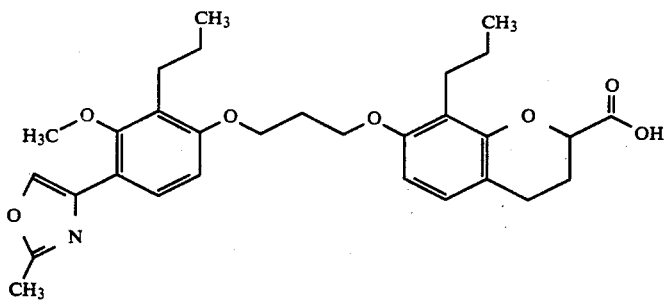

The compound of Example 13 (45 mg, 77 μmol) was combined with 3 mL of 4:1 methanol/THF and 0.3 mL 1N lithium hydroxide, and the reaction was allowed to proceed at room temperature for 1.5 hr. The reaction mixture was poured into ethyl acetate/water, and the ethyl acetate layer was washed with brine, dried over sodium sulfate, and concentrated to give the product; mp 111–115° C. High resolution mass spectrum, m/e 524.2669 (calculated for $C_{30}H_{38}NO_7$ (M+H), 524.2648).

EXAMPLE 15

Methyl 7-[3-[4-(2-bromo-1-oxoethyl)-3-methoxy-2-(2-propenyl)phenoxy]propoxy]-3,4-dihydro-8-propyl-2H-1-benzopyran-2-carboxylate

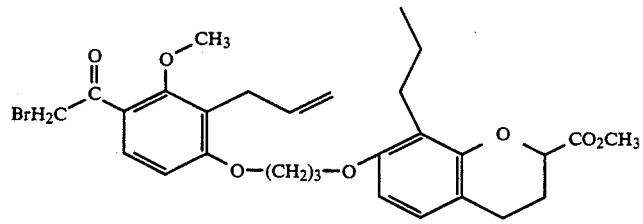

Methyl 7-[3-(4-acetyl-3-methoxy-2-(2-propenyl)-phenoxy) propoxy]-3,4-dihydro-8-propyl-2H-1-benzopyran-2-carboxylate (0.156 g, 0.314 mmol) in 1 mL chloroform was added to 0.134 g (0.60 mmol) cupric bromide in 1 mL hot ethyl acetate, and the mixture was refluxed for 3 hr. The mixture was stirred with Norit A ™ activated carbon, filtered, and concentrated under vacuum. Flash chromatography using 15:1 to 10:1 hexane/ethyl acetate as eluant afforded the product (59 mg, 0.103 mmol, 33% yield).

EXAMPLE 16

Methyl 3,4-dihydro-7-[3-[3-methoxy-2-(2-propenyl)-4-(4-thiazolyl)phenoxy]-propoxy]-8-propyl-2H-1-benzopyran-2-carboxylate

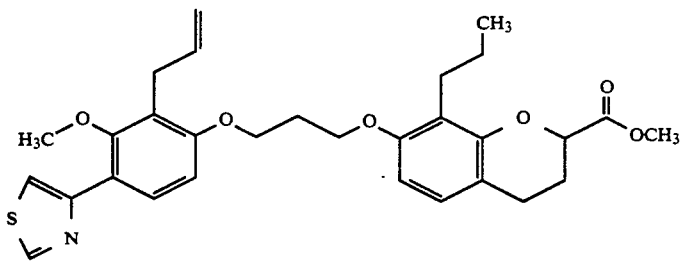

Formamide (0.15 mL, 4.3 mmol) and phosphorus pentasulfide (0.33 g, 0.73 mmol) in 15 mL dioxane were refluxed for 2 hr., and 4 mL of this solution was added to 59 mg of the compound of Example 15 in 2 mL dioxane with 100 mg magnesium carbonate. The reaction mixture was refluxed for 1.75 hr. and poured into ethyl ether/1N sodium hydroxide. The ether layer was washed with brine, dried over sodium sulfate, and concentrated. Flash chromatography on silica gel using 8:1 hexane/ethyl acetate as eluant gave the product (28 mg, 52 μmmol, 51% yield). High resolution mass spectrum, m/e 537.2195 (calculated for $C_{30}H_{35}NO_6S$, 537.2185).

EXAMPLE 17

3,4-dihydro-7-[3-[3-methoxy-2-(2-propenyl)-4-(4-thiazolyl)-phenoxy]propoxy]-8-propyl-2H-1-benzopyran-2-carboxylic acid

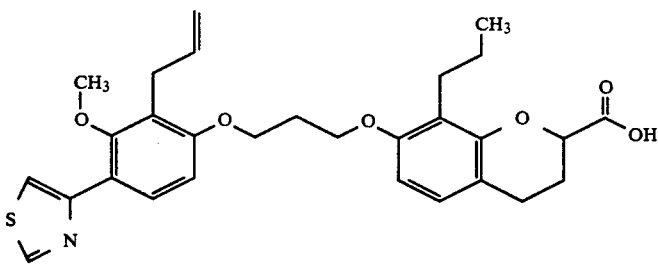

The compound of Example 16 (22 mg, 40.9 μmol), 1 mL 4:1 methanol/THF, and 100 mL 1N lithium hydroxide were stirred at room temperature for 2.75 hours. The mixture was poured into ethyl acetate/water, and the ethyl acetate layer was washed with brine, dried over sodium sulfate and concentrated. Flash chromatography on silica gel using 5:1 hexane/ethyl acetate (1% acetic acid) provided the product (20 mg, 38.1 μmol, 93% yield). High resolution mass spectrum, m/e 479.2114 (calculated for $C_{28}H_{35}NO_4S$ (M-CO$_2$), 479.2130).

EXAMPLE 18

Methyl 7-[3-[4-acetyl-2-(cyclopropylmethyl)-3-methoxyphenoxy]propoxy]-3,4-dihydro-8-propyl-2H-1-benzopyran-2-carboxylate

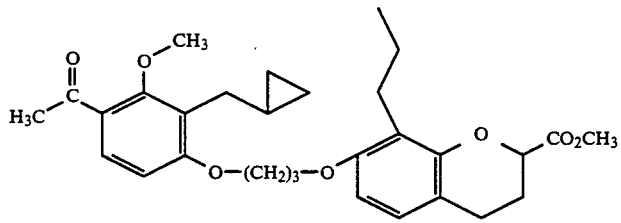

Methyl 7-[3-[4-acetyl-2-(cyclopropylmethyl-3-hydroxyphenoxy]propoxy]-3,4-dihydro-8-propyl-2H-1-benzopyran-2-carboxylate (0.69 g, 1.39 mmol) was stirred in 15 mL THF with 0.20 g (3.57 mmol) potassium hydroxide and 0.34 mL (3.59 mmol) dimethyl sulfate at room temperature for 3.5 hr. The mixture was poured into ethyl ether/water, and the ether layer was washed with brine, dried over sodium sulfate, and concentrated. Flash chromatography on silica gel using 10:1 to 5:1 hexane/ethyl acetate as eluant provided the product (0.705 g, 1.38 mmol, 99% yield). High resolution mass spectrum, m/e 510.2612 (calculated for $C_{30}H_{38}O_7$, 510.2617).

EXAMPLE 19

Methyl 7-[3-[4-(2-bromo-1-oxoethyl)-2-(cyclopropylmethyl)-3-methoxyphenoxy]propoxy]-3,4-dihydro-8-propyl-2H-1-benzopyran-2-carboxylate

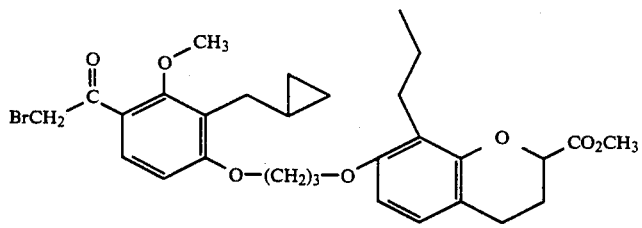

The compound of Example 18 (0.147 g, 0.288 mmol) in 1 mL chloroform was added to 0.125 g (0.45 mmol) of cupric bromide in 1 mL hot ethyl acetate, and the mixture was refluxed for 3 hr. The mixture was stirred with Norit A ™ activated carbon, filtered, and concentrated. Flash chromatography on silica gel using 15:1 to 10:1 hexane/ethyl acetate as eluant provided the product (0.107 g, 0.18 mmol, 63% yield).

EXAMPLE 20

Methyl 7-[3-[2-cyclopropylmethyl)-3-methoxy-4-(4-thiazolyl)phenoxy]propoxy]-3,4-dihydro-8-propyl-2H-1-benzopyran-2-carboxylate

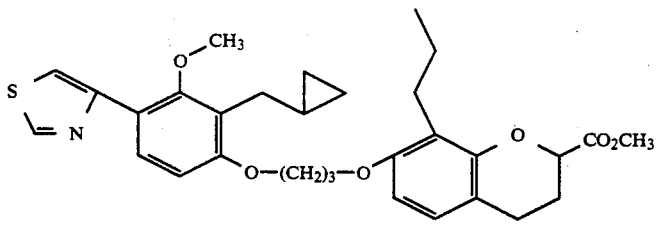

Formamide (0.15 ml, 4.3 mmol) and phosphorus pentasulfide (0.33 g, 0.73 mmol) in 15 ml of dioxane were refluxed for 2 hours, and 4 mL of the solution was added to the compound of Example 19 (0.107 g) in 2 mL of dioxane with 100 mg magnesium carbonate. The mixture was refluxed for 1.75 hr. then poured into ethyl ether/1N sodium hydroxide. The ether layer was washed with brine, dried over sodium sulfate, and concentrated. Flash chromatography using 8:1 hexane/ethyl acetate as eluant provided the product (50 mg, 90.6 μmol, 50% yield). High resolution mass spectrum, m/e 551.2346 (calculated for $C_{31}H_{37}NO_6S$, 551.2341).

EXAMPLE 21

7-[3-[2-(Cyclopropylmethyl)-3-methoxy-4-(4-thiazolyl)phenoxy]propoxy]-3,4-dihydro-8-propyl-2H-1-benzopyran-2-carboxylic acid

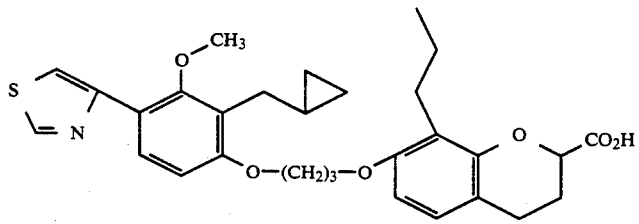

The compound of Example 20 (43 mg, 77.9 μmol) was mixed with 2 mL of 4:1 methanol/THF, and 200 μL 1N lithium hydroxide, and the mixture was allowed to react at room temperature for 2.75 hours. The mixture was poured into ethyl acetate/water, and the ethyl acetate layer was washed with brine, dried over sodium sulfate, and concentrated. Flash chromatography on silica gel using 5:1 hexane/ethyl acetate (1% acetic acid) as eluant provided the product (41 mg, 76.2 μmol, 98% yield). High resolution mass spectrum, m/e 493.2294 (calculated for $C_{29}H_{35}NO_4S$ ($M-CO_2$), 493.2287).

EXAMPLE 22

Methyl 3,4-dihydro-7-[3-[3-methoxy-4-(1-oxo-2-thiocyanatoethyl)-2-propylphenoxy]propoxy]-8-propyl-2H-1-benzopyran-2-carboxylate

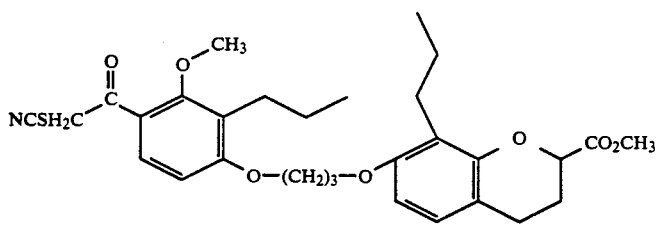

The compound of Example 6 (0.16 g, 0.300 mmol) was mixed with potassium thiocyanate (32 mg, 0.33 mmol) and 3 mL of ethanol, and the reaction mixture was refluxed for 6 hr. The reaction mixture was cooled and poured into ethyl ether/water. The ether layer was washed with water and brine, dried over sodium sulfate, and concentrated under vacuum to give the product.

tion mass spectrum, m/e 569.2438 (calculated for $C_{31}H_{39}NO_7S$, 569.2447).

EXAMPLE 24

3,4-Dihydro-7-[3-[3-methoxy-4-(2-methoxy-4-thiazolyl)-2-propylphenoxy]propoxy]-8-propyl-2H-1-benzopyran-2-carboxylic acid

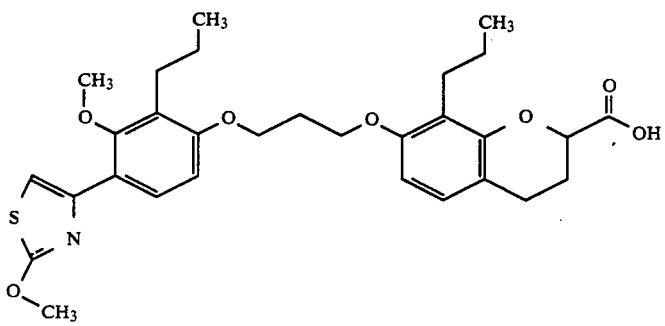

EXAMPLE 23

Methyl 3,4-dihydro-7-[3-[3-methoxy-4-(2-methoxy-4-thiazolyl)-2-propylphenoxy]propoxy]-8-propyl-2H-1-benzopyran-2-carboxylate The compound of Example 23 (20 mg, 35.1 μmol) was added to 2 mL of 4:1 methanol/THF and 0.08 mL of 1N lithium hydroxide, and the reaction was allowed to proceed at room temperature for 2.75 hr. The mixture was poured into ethyl acetate/water, and the ethyl

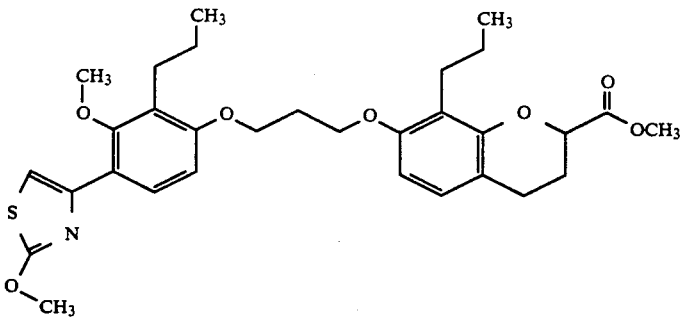

The compound of Example 22 (20 mg, 35.9 μmol) was mixed with 2 mL of methanol and about 10 mg sodium methoxide, and the reaction mixture was held at room temperature for 30 min. The reaction mixture was poured into ethyl ether/water, and the ether layer was washed with brine, dried over sodium sulfate, and concentrated. Flash chromatography on silica gel using 20:1 to 10:1 to 5:1 hexane/ethyl acetate as eluant gave the product (24 mg, 42.1 μmol, 39% yield). High resoluacetate layer was washed with brine, dried over sodium sulfate, and concentrated to give the product (19 mg, 34.1 μmol, 97% yield).

EXAMPLE 25

Methyl 3,4-dihydro-7-[3-[4-(2,3-dihydro-2-thioxo-4-thiazolyl)-3-methoxy-2-propylphenoxy]propoxy]-8-propyl-2H-1-benzopyran-2-carboxylate

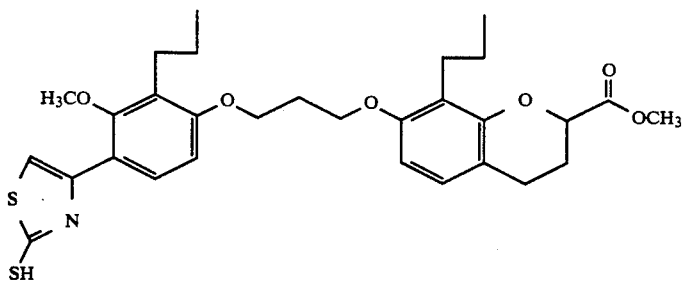

The compound of Example 6 (50 mg, 0.094 mmol) was added to 2.0 ml of ethanol and 0.2 ml of water was added followed by about 12 mg (0.109 mmol) of ammonium dithiocarbamate and the reaction mixture was stirred for four hours at about 50° C. The reaction mixture was poured into ethyl ether/water, and the ether layer was washed with brine, dried over sodium sulfate, and concentrated. Flash chromatography on silica gel using 10:1 to 3:1 hexane/ethyl acetate as eluant gave the product (30 mg, 52.4 μmol, 56% yield). High resolution mass spectrum, m/e 571.2082 (calculated for $C_{30}H_{37}NO_6S_2$, 571.2062).

EXAMPLE 26

3,4-Dihydro-7-[3-[4-(2,3-dihydro-2-thioxo-4-thiazolyl)-3-methoxy-2-propylphenoxy]propoxy]-8-propyl-2H-1-benzopyran-2-carboxylic acid

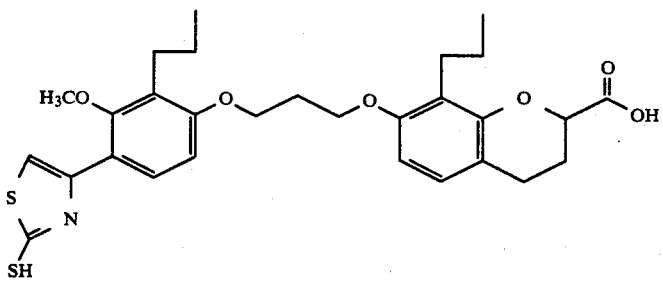

The compound of Example 25 (47 mg, 82.2 μmol) was added to 2.5 ml of 4:1 methanol/THF, and 0.2 ml of 1N lithium hydroxide was added. The mixture was allowed to react at room temperature for 2.5 hours. The reaction mixture was poured into ethyl acetate/water and the ethyl acetate was washed with brine, dried over sodium sulfate and concentrated. Flash chromatography of the residue on silica gel using 7:1 to 5:1 hexane/ethyl acetate (1% acetic acid) as eluant gave the product, melting point 149-51° C., (44 mg, 79 μmol, 96% yield). High resolution mass spectrum, m/e 557.1895 (calculated for $C_{29}H_5NO_6S_2$, 557.1906).

EXAMPLE 27

Methyl 3,4-dihydro-7-[3-[3-methoxy-4-[2-(methylthio)-4-thiazolyl]-2-propylphenoxy]propoxy]-8-propyl-2H-1-benzopyran-2-carboxylate

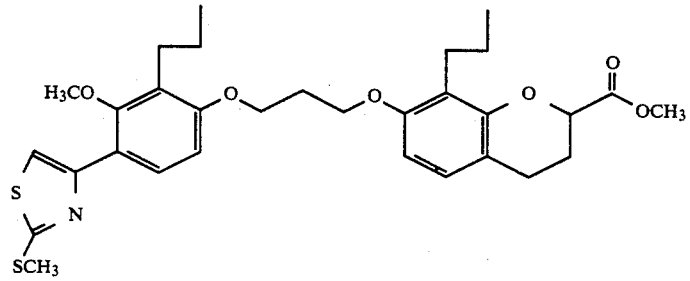

The compound of Example 25 (18 mg, 31.4 μmol) was added to 1.0 ml of nitromethane, and 0.3 ml of methyl iodide was added. The mixture was allowed to react at room temperature for 1 hour. The reaction mixture was poured into ethyl ether/water, and the ether layer was washed with brine, dried over sodium sulfate, and concentrated. The crude product was chromatographed on silica gel using 20:1 to 10:1 hexane/ethyl acetate as eluant to give the product (51 mg, 87.0 μmol, 97.6% yield). High resolution mass spectrum, m/e 585.2223 (calculated for $C_{31}H_{39}N_6S_2$, 585.2219).

EXAMPLE 28

3,4-Dihydro-7-[3-[3-methoxy-4-[2-(methylthio)-4-thiazolyl]-2-propylphenoxy]propoxy]-8-propyl-2H-1-benzopyran-2-carboxylic acid

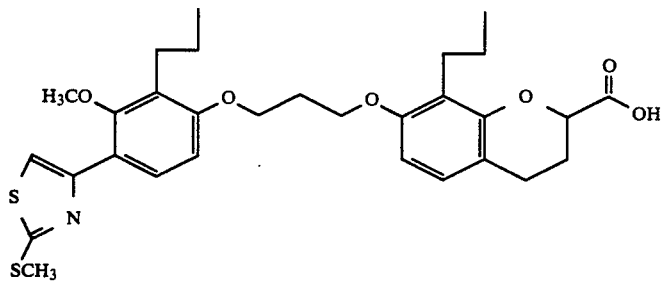

The compound of Example 27 (48 mg, 81.9 μmol) was added to 3.0 ml of 4:1 methanol/THF, and 0.17 ml of 1M lithium hydroxide was added. The mixture was allowed to react at room temperature for 2.75 hours. The reaction mixture was poured into ethyl acetate/water, and the ethyl acetate layer was washed with brine, dried over sodium sulfate and concentrated to give the product (44 mg, 76.9 μmol, 94% yield). High resolution mass spectrum, m/e 527.2159 (calculated for $C_{29}H_{37}NO_4S_2$ (M-$CO_2$), 527.2164).

EXAMPLE 29

3,4-Dihydro-7-[3-[3-methoxy-4-[2-[(phenylmethyl)thio-4-thiazolyl]-2-propylphenoxy]propoxy]-8-propyl-2H-1-benzopyran-2-carboxylic acid

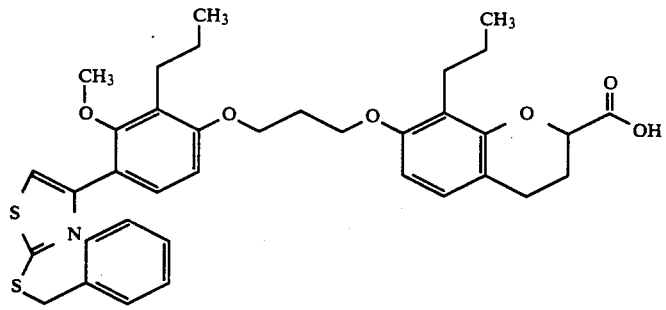

The compound of Example 26 (30 mg, 53.7 μmol) was added to 1.5 ml of nitromethane, 0.5 ml of THF, and 30 ml (0.25 mmol) benzyl bromide. The mixture was allowed to react at room temperature for 1 hour. The reaction mixture was poured into ethyl ether/water, and the ether layer was washed with brine, dried over sodium sulfate, and concentrated under vacuum. Flash chromatography of the residue on silica gel using 10:1 to 7:1 hexane/ethyl acetate (1% acetic acid) gave the product (25 mg, 38.5 μmol, 72% yield). High resolution mass spectrum, m/e 648.2490 (calculated for $C_{36}H_{42}NO_6S_2$ (M+H), 648.2453).

EXAMPLE 30

Methyl 7-[3-(4-acetyl-3-methoxy-2-propylphenoxy)-propoxy]-3,4-dihydro-8-propyl-2H-1-benzopyran-2-propanoate

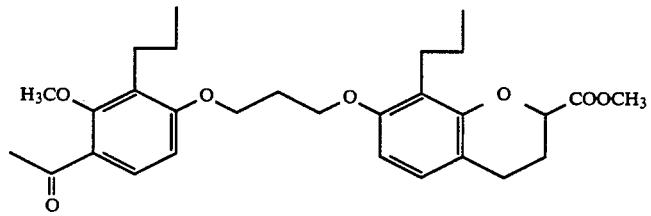

7-[3-(4-Acetyl-3-hydroxy-2-propylphenoxy)propoxy]-3,4-dihydro-8-propyl-2H-1-benzopyran-2-propionic acid (1 mmol) is dissolved in acetone containing 2.5 equivalents of potassium hydroxide and 3 equivalents of dimethyl sulfate. The mixture is heated at 40° C. for about 10 hours then cooled. The solvent is removed in vacuo, and the residue is partitioned between ethyl acetate and water. The organic layer is separated and dried over magnesium sulfate. Removal of the volatiles in vacuo gives the product.

EXAMPLE 31

Methyl 7-[3-(4-(2-bromo-1-oxoethyl)-3-methoxy-2-propylphenoxy)propoxy]-3,4-dihydro-propyl-2H-1-benzopyran-2-carboxylate

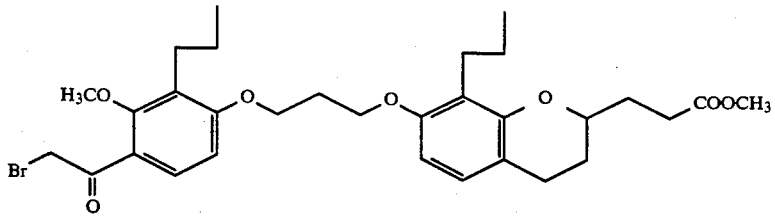

The compound of Example 30 (0.55 g, 0.104 mmol) in 6 ml hot chloroform was added to 0.46 g (2.09 mmol) copper (II) bromide in 6 ml of hot ethyl acetate, and the mixture was refluxed for 3 hours. The mixture was stirred with Norit A ™ activated carbon, filtered, and concentrated. Flash chromatography on silica gel using 15:1 hexane/ethyl acetate provided the product, 0.34 g (0.56 mmol), 54%.

EXAMPLE 32

Methyl 3,4-dihydro-7-[3-[3-methoxy-2-propyl-4-(4-thiazolyl)-phenoxy]propoxy]-8-propyl-2H-1-benzopyran-2-propanoate

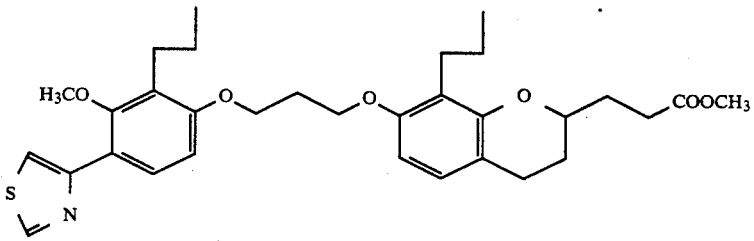

Formamide (0.15 ml, 4.3 mmol), 0.33 g (0.73 mmol) phosphorus pentasulfide and 10 ml of dioxane were refluxed for 1.5 hours, then 7 ml of the solution was added to 0.22 g (0.36 mmol) of the compound of Example 31 and 0.3 g magnesium carbonate in 1 ml of dioxane, and the mixture was refluxed for 1.5 hours. The mixture was poured into ethyl ether/1N sodium hydroxide and the ether layer was washed with brine, dried over sodium sulfate, and concentrated. Flash chromatography using 10:1 to 8:1 hexane/ethyl acetate provided the product (0.16 g, 0.282 mmol), 78%.

EXAMPLE 33

3,4-Dihydro-7-[3-[3-methoxy-2-propyl-4-(4-thiazolyl)phenoxy]propoxy]-8-propyl-2H-1-benzopyran-2-propionic acid

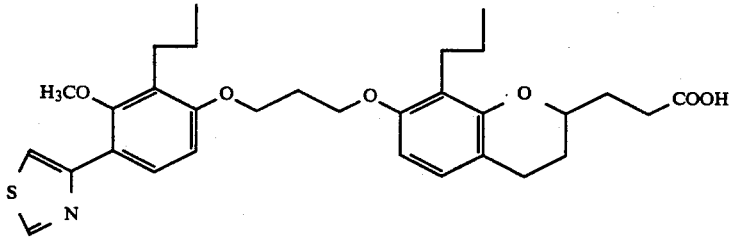

The compound of Example 32 (0.15 g, 0.264 mmol), 8 ml of 4:1 methanol/THF and 0.7 ml of 1M lithium hydroxide were stirred at room temperature for 3 hours. Another 0.3 ml 1M lithium hydroxide was added, and the mixture was stirred at room temperature another 18 hours. The mixture was poured into ethyl acetate/water, and the ethyl acetate layer was washed with brine, dried over sodium sulfate, and concentrated. Reverse phase preparative liquid chromatography using 25/75/1 water/acetonitrile/acetic acid provided the product, 0.113 g (0.204 mmol), 77%, melting point 110–13° C.

Analysis calculated for: $C_{31}H_{39}O_6SN$ (0.8 $H_2O$)
Calculated: C, 65.53; H, 7.20; N, 2.47.
Found: C, 65.49; H, 7.09; N, 2.30.

What is claimed is:

1. A compound of the formula:

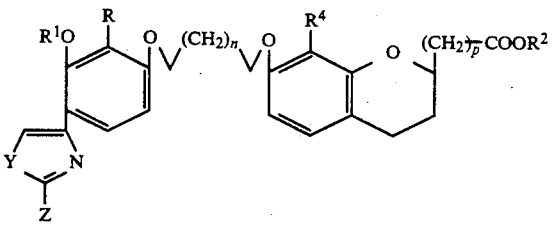

wherein

R represents alkyl having 2 to 6 carbon atoms, alkenyl having 2 to 6 carbon atoms, alkynyl having 2 to 6 carbon atoms, or —$(CH_2)_m$—$R^3$ wherein $R^3$ represents cycloalkyl of 3 to 5 carbons atoms and m is 1 or 2;

$R^1$ represents alkyl having 1 to 4 carbon atoms;

$R^2$ represents hydrogen or alkyl having 1 to 5 carbon atoms;

$R^4$ represents alkyl having 1 to 6 carbon atoms;

n is an integer from 1 to 5;
p is an integer from 0 to 6;
Y represents NH; and
Z represents hydrogen, alkyl having 1 to 4 carbon atoms, alkoxy having 1 to 4 carbon atoms, $NR^4R^5$ wherein $R^4$ and $R^5$ are independently hydrogen or alkyl having 1 to 4 carbon atoms, or $SR^6$ wherein $R^6$ is, hydrogen, benzyl or alkyl having 1 to 4 carbon atoms;

and the stereoisomers and pharmaceutically acceptable salts thereof.

2. A compound according to claim 1 of the formula

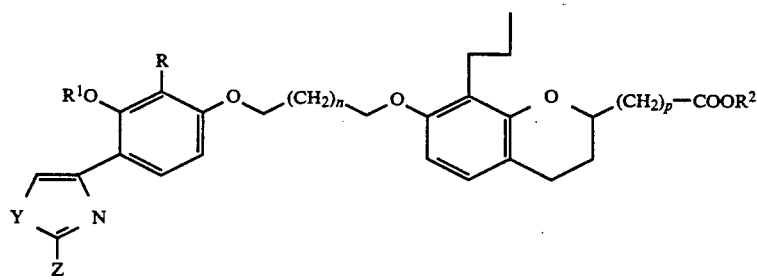

wherein
R represents alkyl having 2 to 4 carbon atoms, alkenyl having 3 to 4 carbon atoms, or cyclopropylalkyl wherein the alkyl moiety has 1 to 2 carbon atoms;
$R^1$ represents methyl or ethyl;
$R^2$ represents hydrogen or alkyl having 1 to 3 carbon atoms;
n is an integer from 1 to 3;
p is an integer from 0 to 4;
Y represents NH; and
Z represents hydrogen, alkyl having 1 to 4 carbon atoms, alkoxy having 1 to 4 carbon atoms, $NH_2$ or $SR^6$ wherein $R^6$ is, hydrogen, benzyl, or alkyl having 1 to 4 carbon atoms; and the stereoisomers and pharmaceutically acceptable salts thereof.

3. A compound according to claim 1 of the formula

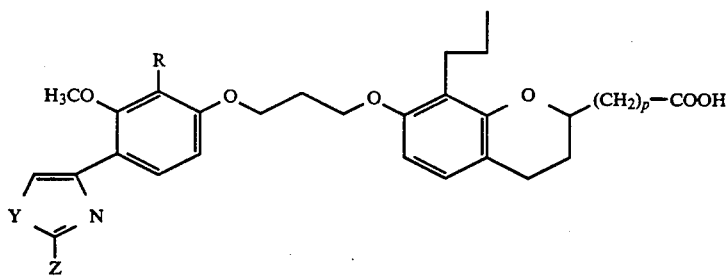

wherein
R represents propyl, 2-propenyl, or cyclopropylmethyl;
p is an integer from 0 to 2;
Y represents NH; and
Z represents hydrogen, $NH_2$, alkyl having 1 to 2 carbon atoms, alkoxy having 1 to 2 carbon atoms, or $SR^6$ wherein $R^6$ is hydrogen, benzyl or methyl;

and the stereoisomers and pharmaceutically acceptable salts thereof.

4. A compound according to claim 3 which is 3,4dihydro-7-[3-[3-methoxy-4-[2-[(phenylmethyl)-thio]-1H-imidazol-4-yl]-2-propylphenoxy]propoxy]-8propyl-2H-1-benzopyran-2-carboxylic acid.

5. A compound according to claim 3 which is 3,4-dihydro-7-[3-[4-(1H-imidazol-4-yl)-3-methoxy-2-propylphenoxy]propoxy-8-propyl-2H-1-benzopyran-2-carboxylic acid.

6. A pharmaceutical composition for treating leukotriene $B_4$ mediated conditions comprising a therapeutically effective amount of a compound of claim 1 and a pharmaceutically acceptable carrier.

7. A pharmaceutical composition for treating inflammatory diseases comprising a therapeutically effective amount of a compound of claim 1 and a pharmaceutically acceptable carrier.

8. A method of treating leukotriene $B_4$ mediated conditions comprising administering to a mammal in need of such treatment a therapeutically effective amount of a compound of claim 1.

9. A method of treating inflammatory diseases comprising administering to a mammal in need of such treatment a therapeutically effective amount of a compound of claim 1.

10. A method according to claim 9 wherein the inflammatory disease is rheumatoid arthritis.

11. A method according to claim 9 wherein the inflammatory disease is psoriasis.

12. A method according to claim 9 wherein the inflammatory disease is inflammatory bowel disease.

13. A method according to claim 9 wherein the inflammatory disease is gout.

14. A method according to claim 9 wherein the inflammatory disease is asthma.

15. A method according to claim 9 wherein the inflammatory disease is multiple sclerosis.

* * * * *

UNITED STATES PATENT AND TRADEMARK OFFICE
CERTIFICATE OF CORRECTION

PATENT NO. : 5,212,198
DATED     : May 18, 1993
INVENTOR(S) : Djuric, et al.

It is certified that error appears in the above-identified patent and that said Letters Patent is hereby corrected as shown below:

Column 4, line 29, reading "with a alkyl" should read -- with an alkyl --.

Column 19, line 35, reading "produce" should read -- product --.

Column 20, line 61, reading "F)ash" should read -- Flash --.

Column 36, line 25, reading the formula

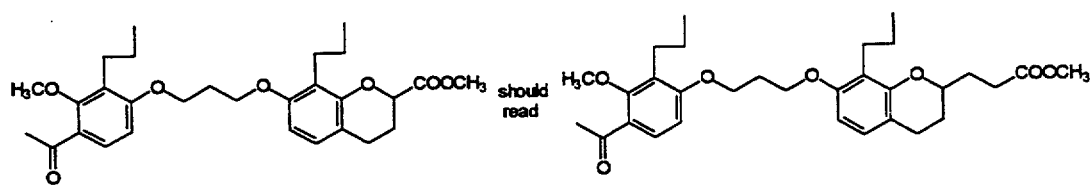 should read 

Column 40, line 5, reading "-8propyl-" should read -- -8-propyl- --.

Signed and Sealed this

Twentieth Day of September, 1994

Attest:

BRUCE LEHMAN

Attesting Officer          Commissioner of Patents and Trademarks